(12) United States Patent
Chen et al.

(10) Patent No.: US 11,623,940 B2
(45) Date of Patent: Apr. 11, 2023

(54) METHODS OF NUCLEIC ACID SYNTHESIS COMPRISING POLYPHOSPHATE CONTAINING SPECIES

(71) Applicant: Nuclera Nucleics Ltd., Cambridge (GB)

(72) Inventors: Michael Chen, Cambridge (GB); Jiahao Huang, Cambridge (GB); Gordon McInroy, Cambridge (GB)

(73) Assignee: Nuclera Nucleics Ltd., Cambridge (GB)

( * ) Notice: Subject to any disclaimer, the term of this patent is extended or adjusted under 35 U.S.C. 154(b) by 395 days.

(21) Appl. No.: 16/646,361

(22) PCT Filed: Sep. 14, 2018

(86) PCT No.: PCT/GB2018/052615
§ 371 (c)(1),
(2) Date: Mar. 11, 2020

(87) PCT Pub. No.: WO2019/053443
PCT Pub. Date: Mar. 21, 2019

(65) Prior Publication Data
US 2020/0270296 A1     Aug. 27, 2020

(30) Foreign Application Priority Data
Sep. 14, 2017   (GB) ..................... 1714827

(51) Int. Cl.
*C12Q 1/68*     (2018.01)
*C07H 21/00*    (2006.01)
*C12Q 1/6806*   (2018.01)
*C12P 19/34*    (2006.01)

(52) U.S. Cl.
CPC .............. *C07H 21/00* (2013.01); *C12P 19/34* (2013.01); *C12Q 1/6806* (2013.01)

(58) Field of Classification Search
CPC ........ C12Q 1/6806; C12P 19/34; C07H 21/00
See application file for complete search history.

(56) References Cited

U.S. PATENT DOCUMENTS 5,990,300 A * 11/1999 Hiatt ................ C12P 19/30
                                                    536/25.31
8,808,989 B1    8/2014 Efcavitch et al.
2016/0108382 A1 4/2016 Efcavitch et al.

FOREIGN PATENT DOCUMENTS

WO       2005/059096 A2    6/2005
WO    WO 2016/139477 A1    9/2016

OTHER PUBLICATIONS

Khandazhinkskaya, et al., "New Nonnucleoside Substrates for Terminal Deoxynucleotidyl Transferase: Synthesis and Dependence of Substrate Properties on Structure," Russian Journal of Bioorganic Chemistry, vol. 31, No. 4, pp. 352-356, 2005.
International Search Report issued in corresponding International Patent Application No. PCT/GB2018/052615 dated Dec. 21, 2018.
Krayevsky et al., "Terminal deoxynucleotidyl transferase: catalysis of DNA (oligodeoxynucleotide) phosphorylation," Pharmacology and Therapeutics, 85 (3): 165-173 (2000).
Arzumanov et al., "Terminal deoxynucleotidyl transferase catalyzes the reaction of DNA phosphorylation," Nucleic Acids Reseach, 28 (5): 1276-1281 (2000).

* cited by examiner

*Primary Examiner* — Jezia Riley
(74) *Attorney, Agent, or Firm* — Morgan, Lewis & Bockius LLP

(57) ABSTRACT

The invention relates to the use of polyphosphate containing species in a method of nucleic acid synthesis, to methods of nucleic acid synthesis, and to the use of kits comprising said polyphosphate containing species. The invention also relates to the use of polyphosphate containing species for the capping of 3'-terminal hydroxyl moieties using terminal transferases.

18 Claims, 2 Drawing Sheets

Lane  1  2  3  4  5  6  7

Lane 1 2 3 4 5 6 7

METHODS OF NUCLEIC ACID SYNTHESIS COMPRISING POLYPHOSPHATE CONTAINING SPECIES

FIELD OF THE INVENTION

The invention relates to the use of polyphosphate containing species in a method of nucleic acid synthesis, to methods of nucleic acid synthesis, and to the use of kits comprising said polyphosphate containing species. The invention also relates to the use of polyphosphate containing species for the capping of 3'-terminal hydroxyl moieties using terminal transferases.

BACKGROUND OF THE INVENTION

Nucleic acid synthesis is vital to modern biotechnology. The rapid pace of development in the biotechnology arena has been made possible by the scientific community's ability to artificially synthesise DNA, RNA and proteins.

Artificial DNA synthesis—a £1 billion and growing market—allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. While the benefits of DNA synthesis are numerous, an oft-mentioned problem prevents the further growth of the artificial DNA synthesis industry, and thus the biotechnology field. Despite being a mature technology, it is practically impossible to synthesise a DNA strand greater than 200 nucleotides in length, and most DNA synthesis companies only offer up to 120 nucleotides. In comparison, an average protein-coding gene is of the order of 2000-3000 nucleotides, and an average eukaryotic genome numbers in the billions of nucleotides. Thus, all major gene synthesis companies today rely on variations of a 'synthesise and stitch' technique, where overlapping 40-60-mer fragments are synthesised and stitched together by PCR (see Young, L. et al. (2004) *Nucleic Acid Res.* 32, e59). Current methods offered by the gene synthesis industry generally allow up to 3 kb in length for routine production.

The reason DNA cannot be synthesised beyond 120-200 nucleotides at a time is due to the current methodology for generating DNA, which uses synthetic chemistry (i.e., phosphoramidite technology) to couple a nucleotide one at a time to make DNA. As the efficiency of each nucleotide-coupling step is 95.0-99.5% efficient, it is mathematically impossible to synthesise DNA longer than 200 nucleotides in acceptable yields. The Venter Institute illustrated this laborious process by spending 4 years and 20 million USD to synthesise the relatively small genome of a bacterium (see Gibson, D. G. et al. (2010) *Science* 329, 52-56).

One type of error that can arise during DNA synthesis is addition failure—when the addition of a monomer unit to the growing polymer chain fails. This type of error leads to deletions in the sequence, and generates contaminating products that are challenging to separate from the target product. Phosphoramidite technology attempts to address this error type with chemical capping of the 5'-hydroxyl (3' to 5' synthesis), most commonly via acetylation with acetic anhydride and 1-methylimidazole. Such approaches are less suitable for enzyme mediated DNA synthesis methods, for two main reasons. Firstly, the 3'-hydroxyl is the capping target (5' to 3' synthesis), which as a secondary alcohol is significantly less reactive than the primary 5'-hydroxyl. Secondly, enzymatic methods are performed in aqueous solution, thus alcohol reactive agents are rapidly inactivated by the presence of water as a solvent.

There is therefore a need to identify novel methods for the capping of 3'-terminal hydroxyl groups to enable error correction strategies in de novo enzymatic DNA synthesis methods, and thus enable the production of higher accuracy DNA products.

SUMMARY OF THE INVENTION

According to a first aspect of the invention, there is provided the use of a polyphosphate containing species as a permanent capping agent in a method of nucleic acid synthesis.

According to a second aspect of the invention, there is provided a method of nucleic acid synthesis, which comprises the steps of:
a. providing an initiator sequence;
b. adding a 3'-reversibly blocked nucleoside triphosphate to said initiator sequence in the presence of a terminal transferase or a functional equivalent or fragment thereof;
c. adding a capping polyphosphate containing species;
d. removal of all reagents from the initiator sequence;
e. cleaving the blocking group from the 3'-reversibly blocked nucleoside triphosphate in the presence of a cleaving agent; and
f. removal of the cleaving agent.

According to a further aspect of the invention, there is provided a kit comprising a terminal transferase and a polyphosphate containing species as described herein, optionally in combination with one or more components selected from: an initiator sequence, one or more 3'-reversibly blocked nucleoside triphosphates, inorganic pyrophosphatase, such as purified, recombinant inorganic pyrophosphatase from Saccharomyces cerevisiae, and a cleaving agent.

According to a further aspect of the invention, there is provided the use of the kit as defined herein in a method of nucleic acid synthesis.

According to a further aspect of the invention, there is provided the use of a terminal transferase and a polyphosphate containing species as defined herein, to add a 3'-$(PO_4^-)R_{10}$ group to a nucleic acid species, wherein the $R_{10}$ group is either absent, or comprises —$(CH_2)_m CH_3$, —$(CH_2)_m CH_2OH$, —$(CH_2)_m CH_2NH_2$, —$NH_2$, or —$(CH_2)_m CH_2SH$, and m is an integer selected from 0 to 6; or $R_{10}$ represents (IA):

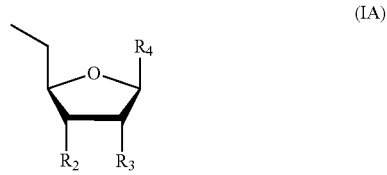

(IA)

wherein $R_2$ and $R_3$ may independently represent —H, —OH, —F, —$OCH_2N_3$, —SH, or —$(CH_2)_m CH_2OH$, m is an integer selected from 0 to 6, and $R_4$ is a canonical nitrogenous base selected from adenine, thymine, guanine, cytosine, and uracil, or a non-canonical nitrogenous base;

or $R_{10}$ represents (IB):

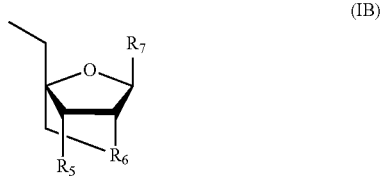

(IB)

wherein $R_5$ represents —H, —OH, —NH$_2$, —N$_3$, —F, —OCH$_3$, —ONH$_2$, —CH$_2$N$_3$, —SH, —(CH$_2$)$_m$CH$_3$, or —(CH$_2$)$_m$CH$_2$OH, m is an integer selected from 0 to 6, $R_6$ represents —O—, —NH—, —S—, or —CH$_2$—, and $R_7$ is a canonical nitrogenous base selected from adenine, thymine, guanine, cytosine, and uracil, or a non-canonical nitrogenous base;

or $R_{10}$ represents (IC):

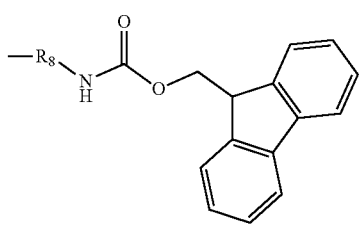

(IC)

wherein $R_8$ represents —(CH$_2$)$_m$—, —(CH$_2$)$_m$C(O)NH (CH$_2$)$_p$, or —(CH$_2$)$_m$[O(CH$_2$)$_2$]$_p$, and m and p are an integer independently selected from 0 to 6.

According to a further aspect of the invention, there is provided the use of a terminal transferase and a tripolyphosphate to phosphorylate the 3'-end of a nucleic acid species.

DETAILED DESCRIPTION OF THE INVENTION

Figure 1:
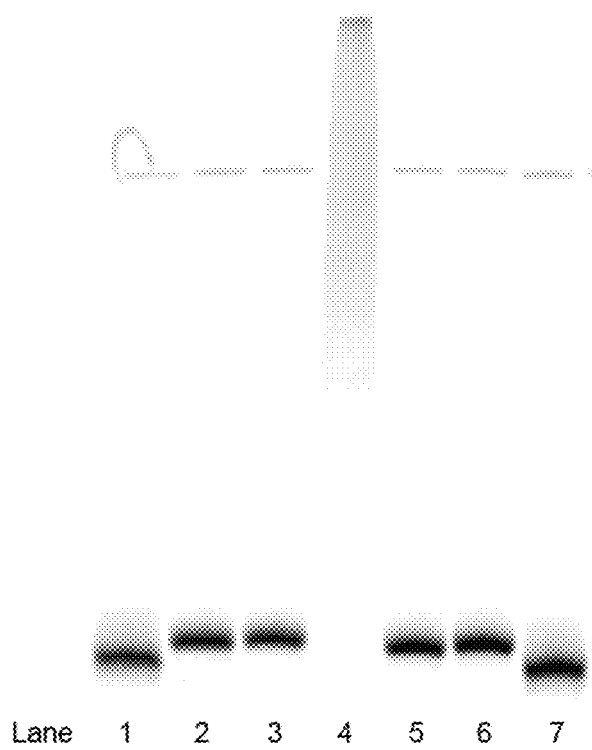
FIG. 1: Incorporation of dideoxynucleoside triphosphates by a terminal transferase prevents subsequent DNA synthesis. Lane 1: initiator sequence; Lane 2: dideoxyadenosine triphosphate addition; Lane 3: dideoxythymidine triphosphate addition; Lanes 4-6: duplicates of lanes 1-3 exposed to dCTP tailing conditions; Lane 7: initiator sequence. While dCTP tailing leads to the formation of a range of higher molecular weight products (Lane 4), prior treatment with a terminal transferase and dideoxynucleoside triphosphate prevents the formation of such higher molecular weight species (Lanes 5 and 6).

The addition step of de novo enzymatic DNA synthesis involves the enzyme-mediated addition of a modified nucleoside triphosphate to a growing oligonucleotide strand. Most commonly a terminal transferase enzyme is employed to add a reversibly terminated nucleoside triphosphate to a growing oligonucleotide strand. If the terminal transferase fails to add a reversibly terminated nucleoside triphosphate to the strand, an error occurs. The error will manifest as a deletion product, predominantly of length L-1, where L is the target length. L-1 products are challenging to separate from full-length products. Capping an addition failure renders the growing strand permanently incompatible with further addition, thus reducing the prevalence of erroneous products of near full-length. Reducing the prevalence of errors in a product pool is of significant industrial value, as errors reduce the efficacy of DNA products in downstream applications and thus increase costs.

The present inventors have devised a novel capping method for aqueous de novo enzymatic DNA synthesis. This method prevents sequences that suffer addition failure from participating in further addition cycles by blocking the terminal 3'-hydroxyl with a capping phosphate moiety or through formation of a phosphodiester bond to a capping species.

3'-phosphate moieties are known in the literature as efficient means of blocking enzymatic activity. Oligonucleotides with 3'-phosphates are routinely produced through the use of controlled pore glass supports such as 3'-phosphate SynBase (Link Technologies Ltd.) in phosphoramidite synthesis. 3'-phosphates find use (amongst other 3' modifications such as 3'-propanol, 3'-propyl, 3'-OMe, etc.) as polymerase chain amplification reaction (PCR) blockers on fluorogenic probes, as such probes must emphatically not act as PCR primers. Notably, phosphoramidite synthesis proceeds in the 3' to 5' direction (the opposite direction to both nature, and de novo enzymatic DNA synthesis), thus the phosphate is installed via attachment to the solid support. The 3'-phosphate moiety is not employed as a capping agent during phophoramidite synthesis methodology.

Polyphosphate Containing Species

The novel use and method presented herein involves the enzymatic addition of a polyphosphate containing species to an addition failure strand, such that the resultant species is rendered incompatible with future additions, i.e., the addition failure strand is "permanently capped".

Therefore, according to a first aspect of the invention, there is provided the use of a polyphosphate containing species as a permanent capping agent in a method of nucleic acid synthesis.

In one embodiment, the polyphosphate containing species is a triphosphate containing species.

References herein to "polyphosphate containing species" refer to a molecule containing more than one tetrahedral phosphate (PO$_4$) unit which are linked together by sharing oxygen centres (e.g., see formula (II)). They can adopt linear or cyclic ring structures. A "triphosphate containing species" refers to a molecule containing three phosphate units. As used herein, the polyphosphate containing species may be referred to as a "capping polyphosphate containing species" because it functions to cap an oligonucleotide during nucleic acid synthesis.

References herein to "permanent capping agent" refer to an agent which is able to prevent further addition to the nucleic acid sequence. This may be achieved by adding a "cap" to the 3'-terminus of the oligonucleotide so that it is no longer a substrate for further enzymatic synthesis. In particular, the permanent capping agent is not susceptible to cleavage, in particular by the cleaving agent described herein. Therefore, when in use in methods of the invention, the permanent capping agent is used in addition to 3'-reversibly blocked nucleoside triphosphates to prevent stands which have undergone an addition failure from proceeding further. Such a capping agent may contain an irreversible 3'-blocking group, for example dNTPs where the 3'-OH group can neither be exposed nor uncovered by cleavage.

Surprisingly, the present inventors have identified that some terminal transferases, including engineered terminal deoxynucleotidyl transferases (see WO2016/128731) are able to incorporate polyphosphate containing species, such as sodium tripolyphosphate. This provides an enzymatic method for 3'-phosphorylation of DNA and RNA oligonucleotides, and thus provides a method for the 3' capping of oligonucleotides in de novo enzymatic DNA synthesis. Tripolyphosphates are produced industrially on a large scale due to their use in many applications, including their use as detergents and food preservatives.

In one embodiment, the polyphosphate containing species comprises a compound of formula (I):

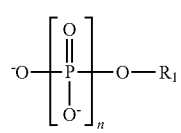

wherein n is an integer selected from 2 to 10; and
wherein $R_1$ is either absent, or comprises —$(CH_2)_mCH_3$, —$(CH_2)_mCH_2OH$, $(CH_2)_mCH_2NH_2$, —$NH_2$, or —$(CH_2)_mCH_2SH$, and m is an integer selected from 0 to 6;
or $R_1$ represents (IA):

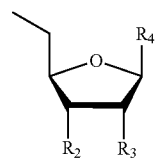

wherein $R_2$ and $R_3$ may independently represent —H, —OH, —$NH_2$, —$N_3$, —F, $OCH_3$, —$ONH_2$, —$OCH_2N_3$, —SH, —$(CH_2)_mCH_3$, or —$(CH_2)_mCH_2OH$, m is an integer selected from 0 to 6 and $R_4$ is a canonical nitrogenous base selected from adenine, thymine, guanine, cytosine, and uracil, or a non-canonical nitrogenous base;
or $R_1$ represents (IB):

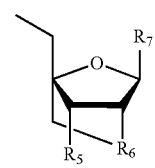

wherein $R_5$ represents —H, —OH, —$NH_2$, —$N_3$, —F, —$OCH_3$, —$ONH_2$, —$CH_2N_3$, —SH, —$(CH_2)_mCH_3$, or —$(CH_2)_mCH_2OH$, m is an integer selected from 0 to 6, $R_6$ represents —O—, —NH—, —S—, or —$CH_2$—, and $R_7$ is a canonical nitrogenous base selected from adenine, thymine, guanine, cytosine, and uracil, or a non-canonical nitrogenous base;
or $R_1$ represents (IC):

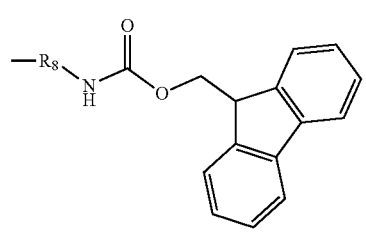

wherein $R_8$ represents —$(CH_2)_m$, —$(CH_2)_mC(O)NH(CH_2)_p$, or —$(CH_2)_m[O(CH_2)_2]_p$, and m and p are integers independently selected from 0 to 6.

In a further embodiment, n is an integer selected from 2 to 5. In a yet further embodiment, n is 3 (i.e. a triphosphate containing species).

In a further embodiment, the polyphosphate containing species comprises a compound of formula (II):

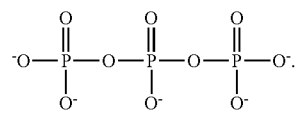

Formula (II) represents a tripolyphosphate species (i.e., when $R_1$ of formula (I) is absent and n is 3). In a further embodiment, the tripolyphosphate species comprises sodium tripolyphosphate.

In a further embodiment, the polyphosphate containing species comprises a compound of formula (III):

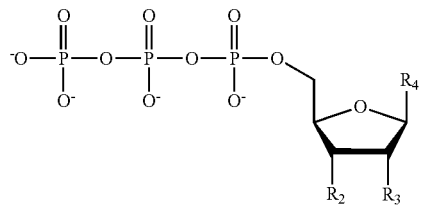

wherein $R_2$ and $R_3$ may independently represent —H, —OH, —$NH_2$, —$N_3$, —F, $OCH_3$, —$ONH_2$, —$OCH_2N_3$, —SH, —$(CH_2)_mCH_3$, or —$(CH_2)_mCH_2OH$, m is an integer selected from 0 to 6 and $R_4$ is a canonical nitrogenous base selected from adenine, thymine, guanine, cytosine, and uracil, or a non-canonical nitrogenous base.

In a yet further embodiment, $R_2$ and $R_3$ may independently represent —H, —OH, —F, —$OCH_2N_3$, —SH, or —$(CH_2)_mCH_2OH$.

In a yet further embodiment, the polyphosphate containing species comprises a compound of formula (III) wherein $R_2$ and $R_3$ represent —H, and $R_4$ is a canonical nitrogenous base selected from adenine, thymine, guanine, cytosine, and uracil, or a non-canonical nitrogenous base. In this embodiment, it will be understood that the polyphosphate containing species is a dideoxynucleoside triphosphate. Incorporation of the dideoxynucleoside triphosphate prevents further oligonucleotide synthesis, as the 3'-hydroxyl required for formation of the subsequent phosphodiester bond is not present.

In a further embodiment, the polyphosphate containing species is a locked nucleoside triphosphate. Therefore, in a further embodiment, the polyphosphate containing species comprises a compound of formula (IV):

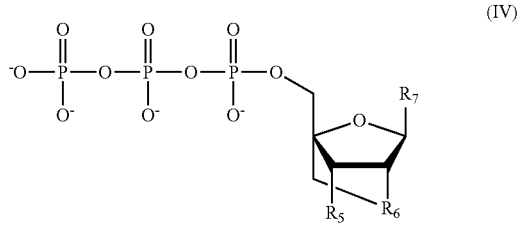

(IV)

wherein $R_5$ represents —H, —OH, —NH$_2$, —N$_3$, —F, —OCH$_3$, —ONH$_2$, —CH$_2$N$_3$, —SH, —(CH$_2$)$_m$CH$_3$, or —(CH$_2$)$_m$CH$_2$OH, m is an integer selected from 0 to 6, $R_6$ represents —O—, —NH—, —S—, or —CH$_2$—, and $R_7$ is a canonical nitrogenous base selected from adenine, thymine, guanine, cytosine, and uracil, or a non-canonical nitrogenous base.

Unlike most polymerases, terminal transferases primarily depend upon the triphosphate groups of their substrates for binding, rather than both the triphosphate and nucleoside moieties. As such, some terminal transferases are able to incorporate triphosphate containing species with only minimal alkyl residues rather than a nucleoside (see, Jasko et al. (2007) *Nucleoside, Nucleotides and Nucleic Acids* 26:323-334; and Crespan et al. (2005) *Nucleic Acids Research* 33:4117-4127).

Therefore, in one embodiment, the polyphosphate containing species comprises a compound of formula (V):

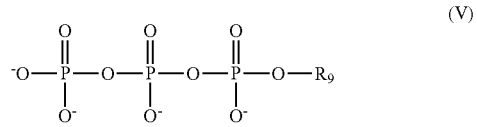

(V)

wherein $R_9$ represents —(CH$_2$)$_m$CH$_3$, —(CH$_2$)$_m$CH$_2$OH, —(CH$_2$)$_m$CH$_2$NH$_2$, —NH$_2$, or —(CH$_2$)$_m$CH$_2$SH, and m is an integer selected from 0 to 6.

In one embodiment, the polyphosphate containing species comprises a compound of formula (VI):

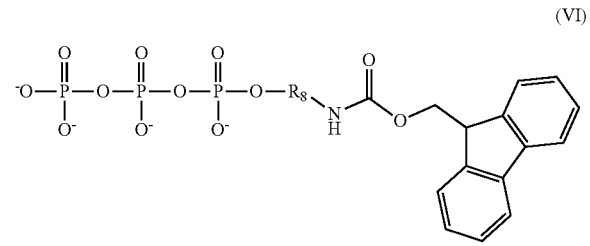

(VI)

wherein $R_8$ represents —(CH$_2$)$_m$, —(CH$_2$)$_m$C(O)NH (CH$_2$)$_p$, or —(CH$_2$)$_m$[O(CH$_2$)$_2$]$_p$, and m and p are an integer independently selected from 0 to 6.

Enzymes

In one embodiment, the polyphosphate containing species is incorporated by an enzyme. In a further embodiment, the enzyme is a terminal transferase, or functional equivalent or fragment thereof.

In one embodiment, the terminal transferase is selected from a terminal deoxynucleotidyl transferase (TdT) enzyme, DNA polymerase beta, DNA polymerase lambda, DNA polymerase theta or RNA uridylyl transferase.

In one embodiment, the enzyme is an RNA polymerase, such as poly(U) polymerase and poly(A) polymerase. It will be understood that these enzymes display terminal transferase like activity and therefore can be classed as a "functional equivalent" of a terminal transferase.

In one embodiment, the terminal transferase is a terminal deoxynucleotidyl transferase (TdT) enzyme, or functional equivalent or fragment thereof. Exemplary TdT enzymes are described in WO2016/128731.

References herein to "TdT" refer to a terminal deoxynucleotidyl transferase (TdT) enzyme and include references to purified and recombinant forms of said enzyme. TdT is also commonly known as DNTT (DNA nucleotidylexotransferase) and any such terms should be used interchangeably.

In a further embodiment, the TdT enzyme is derived from *Sarcophilus harrisii* (UniProt: G3VQ55). *Sarcophilus harrisii* (also known as the Tasmanian devil) is a carnivorous marsupial of the family Dasyuridae, now found in the wild only on the Australian island state of Tasmania.

In a further embodiment, the TdT enzyme is derived from *Lepisosteus oculatus* (UniProt: W5MK82). *Lepisosteus oculatus* (also known as the spotted gar) is a primitive freshwater fish of the family Lepisosteidae, native to North America from the Lake Erie and southern Lake Michigan drainages south through the Mississippi River basin to Gulf Slope drainages, from lower Apalachicola River in Florida to Nueces River in Texas, USA.

In a further embodiment, the TdT enzyme is derived from *Chinchilla lanigera* (NCBI Reference Sequence: XP_005407631.1; http://www.ncbi.nlm.nih.gov/protein/ 533189443). *Chinchilla lanigera* (also known as the long-tailed chinchilla, Chilean, coastal, common chinchilla, or lesser chinchilla), is one of two species of rodents from the genus *Chinchilla*, the other species being *Chinchilla chinchilla*.

In a further embodiment, the TdT enzyme is derived from from *Otolemur garnettii* (UniProt: A4PCE6). *Otolemur garnettii* (also known as the northern greater galago, Garnett's greater galago or small-eared greater galago), is a nocturnal, arboreal primate endemic to Africa.

In a further embodiment, the TdT enzyme is derived from *Sus scrofa* (UniProt: F1SBG2). *Sus scrofa* (also known as the wild boar, wild swine or Eurasian wild pig) is a suid native to much of Eurasia, North Africa and the Greater Sunda Islands.

In a further embodiment, the TdT enzyme is derived from *Bos taurus* (UniProt: P06526). *Bos taurus* (also known as cattle, or colloquially cows) are the most common type of large domesticated ungulates. They are a prominent modern member of the subfamily Bovinae, are the most widespread species of the genus *Bos*.

It will be understood that the term 'functional equivalent' refers to the polypeptides which are different to the exact sequence of the native protein, but can perform the same function, e.g., catalyse the addition of a nucleoside triphosphate or polyphosphate containing species onto the 3'-end of a DNA strand.

In one embodiment, the terminal deoxynucleotidyl transferase (TdT) enzyme is a non-natural derivative of TdT, such as a functional fragment or homolog described herein.

References herein to 'fragment' include, for example, functional fragments with a C-terminal truncation, or with an N-terminal truncation. Fragments are suitably greater than 10 amino acids in length, for example greater than 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 amino acids in length.

Further modified TdT enzymes are described in GB Patent Application No. 1708503.6.

Methods of Nucleic Acid Synthesis

References herein to a "method of nucleic acid synthesis" include methods of synthesising lengths of DNA (deoxyribonucleic acid) or RNA (ribonucleic acid) wherein a strand of nucleic acid (n) is extended by adding a further nucleotide (n+1). In one embodiment, the nucleic acid is DNA. In an alternative embodiment, the nucleic acid is RNA.

References herein to "method of DNA synthesis" refer to a method of DNA strand synthesis wherein a DNA strand (n) is extended by adding a further nucleotide (n+1).

Current synthetic methods for coupling nucleotides to form sequence-specific DNA have reached asymptotic length limits, therefore a new method of de novo DNA synthesis is required. Synthetic DNA synthesis methods also have the disadvantage of using toxic organic solvents and additives (e.g., acetonitrile, acetic anhydride, trichloroacetic acid, pyridine, etc.), which are harmful to the environment.

An alternative, enzymatic method of nucleic acid synthesis is desirable, as previously described in WO2016/128731. The described enzymatic approach is able to produce DNA strands beyond the 120-200 nucleotide limit of current synthetic DNA synthesis methods. Furthermore, this enzymatic method avoids the need to use strong organic solvents which may be harmful to the environment.

Therefore, according to a second aspect of the invention, there is provided a method of nucleic acid synthesis, which comprises the steps of:
 a. providing an initiator sequence;
 b. adding a 3'-reversibly blocked nucleoside triphosphate to said initiator sequence in the presence of a terminal transferase or a functional equivalent or fragment thereof;
 c. adding a capping polyphosphate containing species;
 d. removal of all reagents from the initiator sequence;
 e. cleaving the blocking group from the 3'-reversibly blocked nucleoside triphosphate in the presence of a cleaving agent; and
 f. removal of the cleaving agent.

In one embodiment, step (d) comprises removal of deoxynucleoside triphosphates, the terminal transferase and the capping polyphosphate containing species.

After the addition reaction in step (b), a capping polyphosphate containing species (as described herein) is added to the reaction mixture. Any initiator sequences which have not undergone addition will not be 3'-reversibly blocked and therefore will be capped, i.e., the addition failure strand is capped. This prevents the addition failure stand from incorporating any further nucleoside triphosphates if steps (b) to (f) are repeated. Therefore, step (c) comprises adding a capping polyphosphate containing species to any initiator sequences that did not undergo addition of the 3'-reversibly blocked nucleoside triphosphate in step (b).

The addition of the capping polyphosphate containing species may be done using the same terminal transferase present in the DNA synthesis addition step (i.e. step (b)). Therefore, in this embodiment, no further enzyme needs to be added in step (c). The method therefore has the advantage of not requiring the use of multiple enzymes.

In an alternative embodiment, an enzyme is added during step (c) (i.e., a different enzyme to the step (b) terminal transferase) to incorporate the capping polyphosphate containing species into initiator sequences that did not undergo addition in step (b).

Step (c) may be performed by simply adding the capping polyphosphate containing species to the addition mixture of step (b). Alternatively, the addition mixture in step (b) is removed prior to step (c) and step (c) is performed by adding a new mixture comprising the capping polyphosphate containing species and a terminal transferase (i.e. without the 3'-reversibly blocked nucleoside triphosphate).

It will be understood that the cleaving agent added in step (e) does not cleave the cap added by the capping polyphosphate containing species. Therefore, only initiator strands which have successfully added a 3'-reversibly blocked nucleoside triphosphate will have the blocking group cleaved to allow the stand to undergo further nucleotide addition.

It will be understood that steps (b) to (f) of the method may be repeated multiple times to produce a DNA or RNA strand of a desired length. Therefore, in one embodiment, greater than 1 nucleotide is added to the initiator sequence, such as greater than 5, 10, 20, 30, 40, 50, 60, 70, 80, 90, 100, 110 or 120 nucleotides are added to the initiator sequence by repeating steps (b) to (e). In a further embodiment, greater than 200 nucleotides are added, such as greater than 300, 400, 500, 600, 700, 800, 900, 1000, 1250, 1500, 1750, 2000, 2250, 2500, 2750, 3000, 4000, 5000, 6000, 7000, 8000, 9000 or 10000 nucleotides.

3'-Reversibly Blocked Nucleoside Triphosphates

References herein to 'nucleoside triphosphates' refer to a molecule containing a nucleoside (i.e. a base attached to a deoxyribose or ribose sugar molecule) bound to three phosphate groups. Examples of nucleoside triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of nucleoside triphosphates that contain ribose are: adenosine triphosphate (ATP), guanosine triphosphate (GTP), cytidine triphosphate (CTP) or uridine triphosphate (UTP). Other types of nucleosides may be bound to three phosphates to form nucleoside triphosphates, such as naturally occurring modified nucleosides and artificial nucleosides.

Therefore, references herein to '3'-reversibly blocked nucleoside triphosphates' refer to nucleoside triphosphates (e.g., dATP, dGTP, dCTP or dTTP) which have an additional group on the 3' end which prevents further addition of nucleotides, i.e., by replacing the 3'-OH group with a protecting group, but which can be subsequently removed by a cleaving agent.

It will be understood that references herein to '3'-reversible block', '3'-reversible blocking group' or '3'-reversible protecting group' refer to the group attached to the 3' end of the nucleoside triphosphate which prevents further nucleotide addition but may be removed by a cleaving agent. The present method uses reversible 3'-blocking groups which can be removed by cleavage to allow the addition of further nucleotides.

There exist several documented reversible protecting groups, such as azidomethyl, aminoxy, and allyl, which can be applied to the method described herein. Examples of suitable protecting groups are described in *Greene's Protective Groups in Organic Synthesis*, (Wuts, P. G. M. & Greene, T. W. (2012) 4th Ed., John Wiley & Sons).

In one embodiment, the 3'-reversibly blocked nucleoside triphosphate is blocked by a reversible protecting group.

Therefore, in one embodiment, the 3'-reversibly blocked nucleoside triphosphate is blocked by either a 3'-O-methyl, 3'-azido, 3'-O-azidomethyl, 3'-aminoxy or 3'-O-allyl group. In a further embodiment, the 3'-reversibly blocked nucleoside triphosphate is blocked by either a 3'-O-azidomethyl, 3'-aminoxy or 3'-O-allyl group. In an alternative embodiment, the 3'-reversibly blocked nucleoside triphosphate is blocked by either a 3'-O-methyl or 3'-azido group.

Cleaving Agent

References herein to 'cleaving agent' refer to a substance which is able to cleave the 3'-reversible blocking group from the 3'-reversibly blocked nucleoside triphosphate.

The 3'-reversible blocking groups described herein may all be quantitatively removed in aqueous solution with documented compounds which may be used as cleaving agents (for example, see: Wuts, P. G. M. & Greene, T. W. (2012) 4th Ed., John Wiley & Sons; Hutter, D. et al. (2010) *Nucleosides Nucleotides Nucleic Acids* 29, 879-895; EP 1560838 and U.S. Pat. No. 7,795,424).

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-reversible nucleotide blocking group used. For instance, tris(2-carboxyethyl)phosphine (TCEP) can be used to cleave a 3'-O-azidomethyl group, palladium complexes can be used to cleave a 3'-O-allyl group, or sodium nitrite can be used to cleave a 3'-aminoxy group. Therefore, in one embodiment, the cleaving agent is selected from: tris(2-carboxyethyl) phosphine (TCEP), a palladium complex or sodium nitrite.

In one embodiment, the cleaving agent is added in the presence of a cleavage solution comprising a denaturant, such as urea, guanidinium chloride, formamide or betaine. The addition of a denaturant has the advantage of being able to disrupt any undesirable secondary structures in the DNA. In a further embodiment, the cleavage solution comprises one or more buffers. It will be understood by the person skilled in the art that the choice of buffer is dependent on the exact cleavage chemistry and cleaving agent required.

Initiator Sequences

References herein to an 'initiator sequence' refer to a short oligonucleotide with a free 3'-end which the 3'-reversibly blocked nucleoside triphosphate can be attached to. In one embodiment, the initiator sequence is a DNA initiator sequence. In an alternative embodiment, the initiator sequence is an RNA initiator sequence.

References herein to a 'DNA initiator sequence' refer to a small sequence of DNA which the 3'-reversibly blocked nucleoside triphosphate can be attached to, i.e. DNA will be synthesised from the end of the DNA initiator sequence.

In one embodiment, the initiator sequence between 5 and 100 nucleotides long, such as between 10 and 90 nucleotides long, in particular between 5 and 20 nucleotides long. In a further embodiment, the initiator sequence is between 5 and 50 nucleotides long, such as between 5 and 30 nucleotides long (i.e. between 10 and 30), in particular between 5 and 20 nucleotides long (i.e., approximately 20 nucleotides long), more particularly 5 to 15 nucleotides long, for example 10 to 15 nucleotides long, especially 12 nucleotides long.

In one embodiment, the initiator sequence is single-stranded. In an alternative embodiment, the initiator sequence is double-stranded. It will be understood by persons skilled in the art that a 3'overhang (i.e., a free 3'-end) allows for efficient addition.

In one embodiment, the initiator sequence is immobilised on a solid support. This allows the reagents to be removed (in steps (d) and (f)) without washing away the synthesised nucleic acid. The initiator sequence may be attached to a solid support stable under aqueous conditions so that the method can be easily performed via a flow setup.

In one embodiment, the initiator sequence is immobilised on a solid support via a reversible interacting moiety, such as a chemically-cleavable linker, an antibody/immunogenic epitope, a biotin/biotin binding protein (such as avidin or streptavidin), or glutathione-GST tag. Therefore, in a further embodiment, the method additionally comprises extracting the resultant nucleic acid by removing the reversible interacting moiety in the initiator sequence, such as by incubating with proteinase K.

In a further embodiment, the initiator sequence is immobilised on a solid support via a chemically-cleavable linker, such as a disulfide, allyl, or azide-masked hemiaminal ether linker. Therefore, in one embodiment, the method additionally comprises extracting the resultant nucleic acid by cleaving the chemical linker through the addition of tris(2-carboxyethyl)phosphine (TCEP) or dithiothreitol (DTT) for a disulfide linker; palladium complexes for an allyl linker; or TCEP for an azide-masked hemiaminal ether linker.

In one embodiment, the resultant nucleic acid is extracted and amplified by polymerase chain reaction using the nucleic acid bound to the solid support as a template. The initiator sequence could therefore contain an appropriate forward primer sequence and an appropriate reverse primer could be synthesised.

In an alternative embodiment, the immobilised initiator sequence contains at least one restriction site. Therefore, in a further embodiment, the method additionally comprises extracting the resultant nucleic acid by using a restriction enzyme.

The use of restriction enzymes and restriction sites to cut nucleic acids in a specific location is well known in the art. The choice of restriction site and enzyme can depend on the desired properties, for example whether 'blunt' or 'sticky' ends are required. Examples of restriction enzymes include: AluI, BamHI, EcoRI, EcoRII, EcoRV, HaeII, HgaI, HindIII, HinfI, NotI, PstI, PvuII, SalI, Sau3A, ScaI, SmaI, TaqI and XbaI.

In an alternative embodiment, the initiator sequence contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Method Conditions

In one embodiment, the terminal transferase is added in the presence of an extension solution comprising one or more buffers (e.g., Tris or cacodylate), one or more salts (e.g., $Na^+$, $K^+$, $Mg^{2+}$, $Mn^{2+}$, $Cu^{2+}$, $Zn^{2+}$, $Co^{2+}$, etc., all with appropriate counterions, such as $Cl^-$) and inorganic pyrophosphatase (e.g., the *Saccharomyces cerevisiae* homolog). It will be understood that the choice of buffers and salts depends on the optimal enzyme activity and stability.

The use of an inorganic pyrophosphatase helps to reduce the build-up of pyrophosphate due to nucleoside triphosphate hydrolysis. Therefore, the use of an inorganic pyrophosphatase has the advantage of reducing the rate of (1) backwards reaction and (2) strand dismutation. Thus, according to a further aspect of the invention, there is provided the use of inorganic pyrophosphatase in a method of nucleic acid synthesis. In one embodiment, the inorganic pyrophosphatase comprises purified, recombinant inorganic pyrophosphatase from *Saccharomyces cerevisiae*.

In one embodiment, step (b) is performed at a pH range between 5 and 10. Therefore, it will be understood that any buffer with a buffering range of pH 5-10 could be used, for example cacodylate, Tris, HEPES or Tricine, in particular cacodylate or Tris.

In one embodiment, step (e) is performed at a temperature less than 99° C., such as less than 95° C., 90° C., 85° C., 80° C., 75° C., 70° C., 65° C., 60° C., 55° C., 50° C., 45° C., 40° C., 35° C., or 30° C. It will be understood that the optimal temperature will depend on the cleavage agent utilised. The temperature used helps to assist cleavage and disrupt any secondary structures formed during nucleotide addition.

In one embodiment, steps (d) and (f) are performed by applying a wash solution. In one embodiment, the wash solution comprises the same buffers and salts as used in the extension solution described herein. This has the advantage of allowing the wash solution to be collected after step (d) and recycled as extension solution in step (b) when the method steps are repeated.

In one embodiment, the method is performed within a flow instrument, such as a microfluidic or column-based flow instrument. The method described herein can easily be performed in a flow setup which makes the method simple to use. It will be understood that examples of commercially available DNA synthesisers (e.g., MerMade 192E from BioAutomation or H-8 SE from K&A) may be optimised for the required reaction conditions and used to perform the method described herein.

In one embodiment, the method is performed on a plate or microarray setup. For example, nucleotides may be individually addressed through a series of microdispensing nozzles using any applicable jetting technology, including piezo and thermal jets. This highly parallel process may be used to generate hybridization microarrays and is also amenable to DNA fragment assembly through standard molecular biology techniques.

In one embodiment, the method is performed using a printing method, such as inkjet printing.

In one embodiment, the method described herein may also be performed using digital microfluidic methods.

After steps (b) to (f) have been repeated to achieve the desired length, the resultant nucleic acids may be purified to remove any sequences which had an addition failure and therefore were capped. Thus, in one embodiment, the method additionally comprises: (g) purifying the nucleic acid sequences synthesised in steps (a) to (f) by removing any nucleic acid sequences containing a capping polyphosphate containing species. This may be achieved using methods known in the art, for example purification based on length, molecular weight, hydrophobicity, electrostatic charge or electrophoretic mobility to remove any sequences which were capped and therefore would be shorter than the sequences where addition was able to continue. In an alternative embodiment, a label may be incorporated into the capping polyphosphate containing species so that capped sequences may be removed by selecting for the label. Labels may include biotin, azide, alkyne, alkene, and thiol moieties.

In one embodiment, the method additionally comprises amplifying the resultant nucleic acid. Methods of DNA/RNA amplification are well known in the art. For example, in a further embodiment, the amplification is performed by polymerase chain reaction (PCR). This step has the advantage of being able to extract and amplify the resultant nucleic acid all in one step.

In one embodiment, the method is a template independent nucleic acid synthesis method. References herein to a "template independent nucleic acid synthesis method" refer to a method of nucleic acid synthesis which does not require a template DNA/RNA strand, i.e. the nucleic acid can be synthesised de novo.

The template independent nucleic acid synthesis method described herein has the capability to add a nucleic acid sequence of defined composition and length to an initiator sequence. Therefore, it will be understood by persons skilled in the art, that the method described herein may be used as a way to introduce adapter sequences to a nucleic acid library.

If the initiator sequence is not one defined sequence, but instead a library of nucleic acid fragments (for example generated by sonication of genomic DNA, or for example messenger RNA) then this method is capable of de novo synthesis of 'adapter sequences' on every fragment. The installation of adapter sequences is an integral part of library preparation for next-generation library nucleic acid sequencing methods, as they contain sequence information allowing hybridisation to a flow cell/solid support and hybridisation of a sequencing primer.

Therefore, in one embodiment, an adapter sequence is added to the initiator sequence. In a further embodiment, the initiator sequence may be a nucleic acid from a library of nucleic acid fragments.

Kits

According to a further aspect of the invention, there is provided a kit comprising a terminal transferase and a polyphosphate containing species as described herein, optionally in combination with one or more components selected from: an initiator sequence, one or more 3'-reversibly blocked nucleoside triphosphates, inorganic pyrophosphatase, such as purified, recombinant inorganic pyrophosphatase from Saccharomyces cerevisiae, and a cleaving agent.

According to a further aspect of the invention, there is provided the use of a kit in a method of nucleic acid synthesis, wherein said kit comprises a terminal transferase and polyphosphate containing species as described herein, optionally in combination with one or more components selected from: an initiator sequence, one or more 3'-reversibly blocked nucleoside triphosphates, inorganic pyrophosphatase, and a cleaving agent; further optionally together with instructions for use of the kit in accordance with any of the methods defined herein.

Suitably a kit according to the invention may also contain one or more components selected from the group: an extension solution, a wash solution and/or a cleaving solution as defined herein; optionally together with instructions for use of the kit in accordance with any of the methods defined herein.

Utility of 3'-phosphorylation

The 3'-phosphorylated species described herein have utility in methods other than as a permanent cap in nucleic acid synthesis. Few enzymes in nature are capable of phosphorylating the 3'-end of a nucleic acid species. 3'-phosphorylation conveys 3'-exonuclease resistance and typically blocks elongation by a polymerase (including terminal transferases) or ligation by a ligase. Where fluorogenic primers are used to detect the presence of nucleic acid sequences, 3'-phosphorylation is useful to block fluorogenic DNA/RNA primers from being extended. Additionally, 3'-phosphorylation is useful for directional ligation. For example, T3 DNA ligase will catalyse the ligation of an oligonucleotide with a 3'-OH to an oligonucleotide with a 5'-phosphate in the presence of a complementary oligonucleotide splint (double-stranded context). On the other hand, RtcB (an RNA ligase) will catalyse the ligation of a single-stranded oligonucleotide with a 3'-phosphate to a single-stranded oligonucleotide with a 5'-OH. Thus, through the use of ligases capable of ligating either a 5'- or 3'-phosphorylated oligonucleotide species, greater control over ligation-mediated nucleic acid assembly can be achieved.

Therefore, according to a further aspect of the invention, there is provided the use of the polyphosphate containing species as described herein, to add a phosphate containing species to the 3'-end of a nucleic acid species (e.g. a 3'-(PO$_4^-$)R$_{10}$ group as described herein). In a further embodiment of this aspect of the invention, a terminal transferase is used to add the phosphate containing species.

According to a further aspect of the invention, there is provided the use of a terminal transferase and a polyphosphate containing species as described herein, to add a 3'-(PO$_4^-$)R$_{10}$ group to a nucleic acid species, wherein the R$_{10}$ group is either absent, or comprises —(CH$_2$)$_m$CH$_3$, —(CH$_2$)$_m$CH$_2$OH, —(CH$_2$)$_m$CH$_2$NH$_2$, —NH$_2$, or —(CH$_2$)$_m$CH$_2$SH, and m is an integer selected from 0 to 6;

or R$_{10}$ represents (IA):

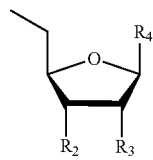

wherein R$_2$ and R$_3$ may independently represent —H, —OH, —F, —OCH$_2$N$_3$, —SH, or —(CH$_2$)$_m$CH$_2$OH, m is an integer selected from 0 to 6, and R$_4$ is a canonical nitrogenous base selected from adenine, thymine, guanine, cytosine, and uracil, or a non-canonical nitrogenous base;

or R$_{10}$ represents (IB):

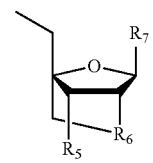

wherein R$_5$ represents —H, —OH, —NH$_2$, —N$_3$, —F, —OCH$_3$, —ONH$_2$, —CH$_2$N$_3$, —SH, —(CH$_2$)$_m$CH$_3$, or —(CH$_2$)$_m$CH$_2$OH, m is an integer selected from 0 to 6, R$_6$ represents —O—, —NH—, —S—, or —CH$_2$—, and R$_7$ is a canonical nitrogenous base selected from adenine, thymine, guanine, cytosine, and uracil, or a non-canonical nitrogenous base;

or R$_{10}$ represents (IC):

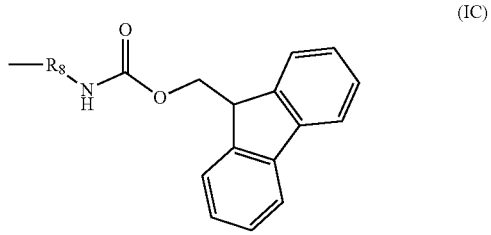

wherein R$_8$ represents —(CH$_2$)$_m$, —(CH$_2$)$_m$C(O)NH (CH$_2$)$_p$, or —(CH$_2$)$_m$[O(CH$_2$)$_2$]$_p$, and m and p are an integer independently selected from 0 to 6.

According to a further aspect of the invention, there is provided the use of a tripolyphosphate to phosphorylate the 3'-end of a nucleic acid species. In one embodiment, the tripolyphosphate is sodium tripolyphosphate.

According to a further aspect of the invention, there is provided the use of a terminal transferase and a tripolyphosphate to phosphorylate the 3'-end of a nucleic acid species. In one embodiment, the tripolyphosphate is sodium tripolyphosphate.

Without being bound by theory, the 3'-phosphate is formed by the terminal transferase-mediated addition of a phosphate group from the tripolyphosphate, where one phosphate group is added to the 3'-terminus and two phosphates are released as a pyrophosphate by-product.

It will be understood that all embodiments described hereinbefore apply to all aspects of the invention.

The following studies and protocols illustrate embodiments of the methods described herein:

EXAMPLE 1

Use of Dideoxynucleoside Triphosphate as a Capping Agent

Data is presented herein which exemplifies the utility of dideoxynucleoside triphosphates as a capping agent by incorporating a dideoxynucleotide using a terminal transferase, and so preventing polymerization of deoxycytidine triphosphate (dCTP) in a subsequent step with terminal transferase (FIG. 1). The initiator strand of length N (lane 1) is converted to an N+1 species through the terminal transferase-mediated addition of dideoxyadenosine triphosphate (ddATP, lane 2) or dideoxythymidine triphosphate (ddTTP, lane 3). When the initiator strand is exposed to terminal transferase in the presence of dCTP, many higher molecular weight products are formed (a smear on the gel) due to the uncontrolled incorporation of dCTP into the initiator strand (lane 4). However, initiator strands pre-treated with ddATP or ddTTP are resistant to incorporation of dCTP when exposed to terminal transferase and dCTP (lanes 5 and 6). Lane 7 is a duplicate of lane 1.

EXAMPLE 2

Use of Tripolyphosphate as a Capping Agent

Figure 2:
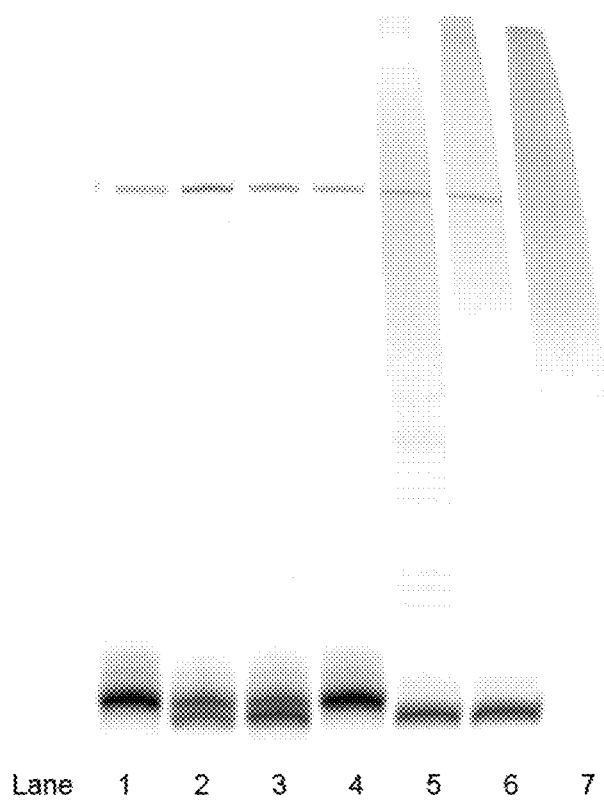
FIG. 2: Incorporation of tripolyphosphate by a terminal transferase prevents subsequent DNA synthesis. Lane 1: initiator sequence; Lane 2: 1 mM sodium tripolyphosphate; Lane 3: 10 mM sodium tripolyphosphate; Lane 4: 50 mM sodium tripolyphosphate; Lanes 5-7: duplicates of lanes 2-4 exposed to dCTP tailing conditions. Reaction products were analysed by denaturing polyacrylamide gel and visualized by an internal FAM dye. An initiator sequence exposed to a terminal transferase and tripolyphosphate is converted to a 3'-phosphorylated initiator sequence (Lanes 2 and 3). Such 3'-phosphorylated initiator sequences are resistant to enzyme mediated DNA polymerisation (Lanes 5 and 6).

Data is presented herein which exemplifies the utility of tripolyphosphate as a capping agent by incorporating a phosphate moiety on the 3'-terminus of an oligonucleotide using a terminal transferase, and so preventing polymerization of dCTP in a subsequent step with terminal transferase (FIG. 2). As demonstrated in lanes 2 and 3 by the appearance of a faster migrating band, following incubation with a terminal transferase and 1 mM or 5 mM tripolyphosphate the initiator strand is partially converted to a new 3'-phosphorylated species. The new species migrates faster on the polyacrylamide gel due to the additional charge presented by the new 3'-phosphate moiety. Lane 4 shows that at 50 mM the terminal transferase mediated phosphorylation does not proceed. Following incubation with the terminal transferase and tripolyphosphate, the mixture was removed. The initiator strand was then incubated with a terminal transferase and canonical dCTP. If a free 3'-hydroxyl is present, terminal transferase will add many dCTP in an uncontrolled fashion to generate higher molecular weight oligonucleotides. Lanes 5 and 6 demonstrate that capping via pre-incubation with 1 mM or 5 mM tripolyphosphate and terminal transferase largely prevents this polymerization. In contrast, lane 7 shows the complete polymerization to higher molecular weight species following a failed capping step.

The invention claimed is:

1. A method of nucleic acid synthesis, which comprises the steps of:
   a. providing an initiator sequence;
   b. adding a 3'-reversibly blocked nucleoside triphosphate to said initiator sequence in the presence of a terminal transferase or a functional equivalent or fragment thereof;
   c. adding a capping polyphosphate containing species to cap any remaining initiator sequence;
   d. removal of the capping reagents from the initiator sequence;
   e. cleaving the blocking group from the added 3'-reversibly blocked nucleoside in the presence of a cleaving agent; and
   f. removal of the cleaving agent,
wherein the polyphosphate containing species comprises a compound of formula (I):

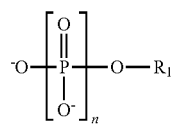

(I)

wherein n is an integer selected from 2 to 10; and
wherein $R_1$ is either absent, or comprises —$(CH_2)_m CH_3$, —$(CH_2)_m CH_2 OH$, —$(CH_2)_m CH_2 NH_2$, —$NH_2$, or —$(CH_2)_m CH_2 SH$, and m is an integer selected from 0 to 6;
or $R_1$ represents (IC):

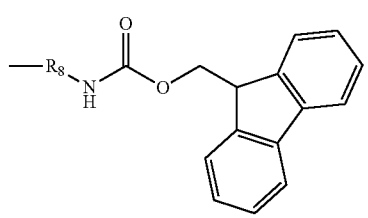

(IC)

wherein $R_8$ represents —$(CH_2)_m$, —$(CH_2)_m C(O)NH(CH_2)_p$, or —$(CH_2)_m [O(CH_2)_2]_p$, and m and p are an integer independently selected from 0 to 6.

2. The method as defined in claim 1, wherein the polyphosphate containing species is incorporated by an enzyme.

3. The method as defined in claim 2, wherein the enzyme is a terminal transferase, or functional equivalent or fragment thereof.

4. The method as defined in claim 1, wherein the polyphosphate containing species is a tripolyphosphate.

5. The method as defined in claim 1, wherein greater than 1 nucleotide is added by repeating steps (b) to (f).

6. The method as defined in claim 1, wherein the 3'-reversibly blocked nucleoside triphosphate is blocked by either a 3'-O-methyl, 3'-azido, 3'-O-azidomethyl, 3'-aminoxy or a 3'-O-allyl group.

7. The method as defined in claim 1, wherein the terminal transferase or functional equivalent or fragment thereof, is added in the presence of an extension solution comprising one or more buffers, one or more salts, and inorganic pyrophosphatase.

8. The method as defined in claim 1, wherein step (b) is performed at a pH range between 5 and 10.

9. The method as defined in claim 1, wherein the cleaving agent is a chemical cleaving agent or an enzymatic cleaving agent.

10. The method as defined in claim 1, wherein steps (d) and (f) are performed by applying a wash solution.

11. The method as defined in claim 1, wherein the method is performed within a flow instrument, or performed on a plate.

12. The method as defined in claim 1, wherein the initiator sequence is between 5 and 50 nucleotides long.

13. The method as defined in claim 1, wherein the initiator sequence is single-stranded or double-stranded.

14. The method as defined in claim 1, wherein the initiator sequence is immobilised on a solid support.

15. The method as defined in claim 1, wherein the initiator sequence contains at least one uridine.

16. The method as defined in claim 1, wherein the capping polyphosphate containing species comprises a compound of formula (V):

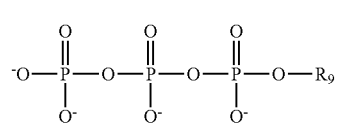

(V)

wherein $R_9$ represents —$(CH_2)_m CH_3$, —$(CH_2)_m CH_2 OH$, —$(CH_2)_m CH_2 NH_2$, —$NH_2$, or —$(CH_2)_m CH_2 SH$, and m is an integer selected from 0 to 6.

17. The method as defined in claim 1, wherein the method is performed on a digital microfluidic device.

18. The method as defined in claim 1, wherein the method is performed using a printing method.

* * * * *